(12) United States Patent
Hwang et al.

(10) Patent No.: US 10,947,231 B2
(45) Date of Patent: Mar. 16, 2021

(54) PROCESSES FOR THE PREPARATION OF SUBSTITUTED TETRAHYDRO BETA-CARBOLINES

(71) Applicant: PTC Therapeutics, Inc., South Plainfield, NJ (US)

(72) Inventors: Peter Seongwoo Hwang, Edison, NJ (US); Young-Choon Moon, Belle Mead, NJ (US); Arasu Tamil, Edison, NJ (US); Hongyan Qi, Plainsboro, NJ (US); Neil Almstead, Princeton, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 16/580,078

(22) Filed: Sep. 24, 2019

(65) Prior Publication Data
US 2020/0017493 A1    Jan. 16, 2020

Related U.S. Application Data

(60) Division of application No. 16/235,068, filed on Dec. 28, 2018, now abandoned, which is a continuation of application No. 13/321,262, filed as application No. PCT/US2010/036273 on May 27, 2010, now abandoned.

(60) Provisional application No. 61/181,652, filed on May 27, 2009.

(51) Int. Cl.
C07D 471/04    (2006.01)

(52) U.S. Cl.
CPC .................. C07D 471/04 (2013.01)

(58) Field of Classification Search
CPC .................................................. C07D 471/04
USPC ............................................................ 546/85
See application file for complete search history.

(56) References Cited

U.S. PATENT DOCUMENTS

| | | | |
|---|---|---|---|
| 3,328,412 A | 6/1967 | Atkinson et al. | |
| 5,206,377 A | 4/1993 | McAfee | |
| 5,314,908 A | 5/1994 | McAfee | |
| 5,500,431 A | 3/1996 | Audia et al. | |
| 5,760,051 A | 6/1998 | Audia et al. | |
| 6,090,945 A | 7/2000 | Audia et al. | |
| 6,093,723 A | 7/2000 | Miao et al. | |
| 6,720,331 B2 | 4/2004 | Yeh et al. | |
| 7,601,840 B2 * | 10/2009 | Moon | A61K 31/5355 546/117 |
| 7,767,689 B2 | 8/2010 | Moon et al. | |
| 7,872,133 B2 | 1/2011 | Ohmoto et al. | |
| 8,076,352 B2 | 12/2011 | Cao et al. | |
| 8,076,353 B2 | 12/2011 | Cao et al. | |
| 8,367,694 B2 | 2/2013 | Moon et al. | |
| 8,372,860 B2 | 2/2013 | Moon et al. | |
| 2003/0040527 A1 | 2/2003 | Yeh et al. | |
| 2004/0116458 A1 | 6/2004 | Sawyer et al. | |
| 2005/0282849 A1 | 12/2005 | Moon et al. | |
| 2007/0254878 A1 | 11/2007 | Cao et al. | |
| 2008/0103164 A1 | 5/2008 | Gudmundsson et al. | |
| 2010/0125065 A1 | 5/2010 | Moon et al. | |
| 2010/0158858 A1 | 6/2010 | Cao et al. | |
| 2010/0179132 A1 | 7/2010 | Moon et al. | |
| 2011/0160190 A1 | 6/2011 | Moon et al. | |
| 2012/0129841 A1 | 5/2012 | Cao et al. | |
| 2012/0202763 A1 | 8/2012 | Almstead et al. | |
| 2019/0135810 A1 | 5/2019 | Hwang et al. | |

FOREIGN PATENT DOCUMENTS

| | | |
|---|---|---|
| EP | 0357122 A2 | 3/1990 |
| EP | 0549916 A2 | 7/1993 |
| FR | 2662940 A1 | 12/1991 |
| JP | 3-287586 | 12/1991 |
| JP | 4275221 | 9/2002 |
| WO | 1991/018604 | 12/1991 |
| WO | 1994/010175 A1 | 5/1994 |
| WO | 1995/026723 | 10/1995 |
| WO | 1997/037658 A1 | 10/1997 |

(Continued)

OTHER PUBLICATIONS

Jun Lu et al. Effect of Trace Amounts of water in the Mobile Phase of Normal-Phase Enantioselective High-Performance Liquid Chromatography on Selectivity and resolution of optical Isomers (Year: 2009).*

(Continued)

*Primary Examiner* — Rita J Desai
(74) *Attorney, Agent, or Firm* — Hoffmann & Baron, LLP

(57) ABSTRACT

Provided herein are improved processes for the synthesis of substituted tetrahydro beta-carboline derivatives. In particular, provided herein are improved processes useful for the preparation of (S)-4-chlorophenyl 6-chloro-1-(4-methoxyphenyl)-3,4-dihydro-1H-pyrido[3,4-b]indole-2(9H)-carboxylate. Formula (I):

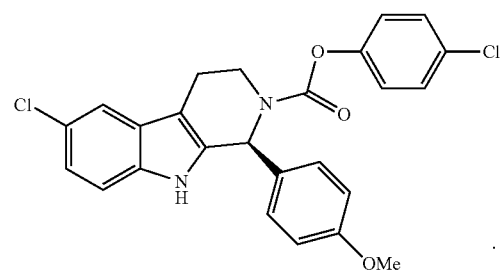

6 Claims, No Drawings

(56) References Cited

FOREIGN PATENT DOCUMENTS

| WO | 2002/062339 | A1 | 8/2002 | | |
|---|---|---|---|---|---|
| WO | 2002/064590 | A2 | 8/2002 | | |
| WO | 2003/033496 | A1 | 4/2003 | | |
| WO | 2003/099821 | A1 | 12/2003 | | |
| WO | 2004/113336 | A1 | 12/2004 | | |
| WO | 2005/007672 | A2 | 1/2005 | | |
| WO | 2005/009370 | A2 | 2/2005 | | |
| WO | 2005/070930 | A2 | 8/2005 | | |
| WO | 2005/089764 | A1 | 9/2005 | | |
| WO | WO-2005089764 | A1 * | 9/2005 | .......... | A61K 31/437 |
| WO | 2005/115470 | A2 | 12/2005 | | |
| WO | 2006/015035 | A1 | 2/2006 | | |
| WO | 2006/058088 | A2 | 6/2006 | | |
| WO | 2006/113703 | A2 | 10/2006 | | |
| WO | 2007/002051 | A1 | 1/2007 | | |

OTHER PUBLICATIONS

Begum et al., 1996, "Chemistry and biological activity of a tryptamine and beta-carboline series of bases", Drug Research; 12(46):1163-1168.
Berrougui et al., 2005, "Cytoxic activity of methanolic extract and two alkaloids extracted from seeds of *Peganum narmala* L", Journal of Natural Remedies; 5(1):41-45.
Boyer et al., 2002, "Small molecule inhibitors of KDR (VEGFR-2) kinase: an overview of structure activity relationships", Current Topics in Medicinal Chemistry; 2(9):973-1000.
Cao et al., 2005, "Synthesis and in vitro cytotoxic evaluation of 1,3-disbstituted and 1,3,9-trisubstituted beta-carboline derivatives", European Journal of Medicinal Chemistry; 40(3):249-257.
Database WPI Accession No. 1992-376264, Abstract of JP 4275221, 1992, Taisho Pharm. Co., Ltd.
Fuhrmann-Benzakein et al., 2000, "Elevated levels of angiogenic cytokines in the plasma of cancer patients", International Journal of Cancer; 85(1):40-45.
Hirawat et al., 2006, "51 Poster Phase 1 single-dose safety, PK, and food-effect study of PTC299, a novel VEGF expression inhibitor for treatment of solid tumors", European Journal of Cancer, Suppl; 4(12):19-20.
Hirawat et al., 2007, "Phase 1 studies assessing the safety, PK, and VEGF-modulating effects of PTC299, a novel VEGF expression inhibitor", Journal of Clinical Oncology ASCO Annual Meeting proceedings Part 1; 25(18s):Abstract 3562.
International Search Report in International application PCT/US2010/036273, dated Jul. 28, 2010.
Ishida et al., 1999, "Antitumor Agents 201. Cytotoxicity of harmine and beta-carboline analogs", Bioorganic & Medicinal Chemistry Letters; 9(23):3319-3324.
Nicolaus et al., 1983, "Symbiotic approach to drug design", Decision Making in Drug Research; 173-186.
Venkov et al., 1999, "Synthesis of 2-acyltetrahydro-β-carbolines by an intramolecular α-amidoalkylation reaction", Synthetic Communications; 29(3):487-494.
Written Opinion of International application PCT/US2010/036273, dated Jul. 28, 2010.
Audia et al., 1996, "Potent, Selective Tetrahydro-beta-carboline Antagonists of the Serotonin 2B (5HT2B) Contractile Receptor in the Rat Stomach Fundus", J. Med. Chem. 39:2773-2780.
Database REAXYS [Online], Elsevier Information Systems GmbH, Frankfurt/Main; XP002675485, Database Accession No. 84862, 230057, 306267 (XRN), accompanied by Fischer, 1897, "Über Harmin und Harmalin," Ber. Dtsch. Chem. Ges. 30(3):2481-2489; Fischer, 1901, "Chemische Studien der Alkaloide der Steppenraute (Peganum Harmala)," Chem. Zentralbl. 72(1):957-959; Partial European Search Report for EP11178488 dated May 9, 2012, p. 2.
Database REAXYS [Online], Elsevier Information Systems GmbH, Frankfurt/Main; XP002675485, Database Accession No. 207280, 3918373 (XRN), accompanied by Fischer, 1914, "Über Harmin und Harmalin," Ber. Dtsch. Chem. Ges. 47:99-107; Partial European Search Report for EP11178488 dated May 9, 2012, p. 3.
Formagio et al., 2009, "Synthesis and antiviral activity of β-carboline derivatives bearing a stubstituted carbohydrazide at C-3 against poliovirus and herpes simplex virus (HSV-1)," Eur. J. Med. Chem. 44:4695-4701.
Hino et al., 1990, "2-Hydroxy-1-substituted-1,2,3,4-tetrahydro-β-carbolines. The Pictet-Spengler Reaction of N-Hydroxytryptamine with Aldehydes," Chem. Pharm. Bull. 38(1):59-64.
Jiang et al., 2003, "Potassium Superoxide as an Alternative Reagent for Winterfeldt Oxidation of β-Carbolines," Organic Letters 5(1):43-46.
Kawashima et al., 1995, "Synthesis and Pharmacological Evaluation of 1,2,3,4-Tetrahydro-β-Carboline Derivatives," Chem. Pharm. Bull. 43(5):783-787.
Kawate et al., 1999, "Chiral Auxiliary Approach to the Asymmetric Pictet-Spengler Reaction of Tryptamines", Heterocycles 50(2):1033-1039.
Lehnert et al., 1994, "DNA topoisomerase II inhibition by substituted 1,2,3,4-tetrahydro-β-carboline derivatives," Biorganic & Medicinal Chemistry Letters 4(20):2411-2416.
McNulty et al., 1991, "Diastereoselective Pictet-Spengler of L-(Boc) prolinal: a biomimetic synthesis of eudistomins H and I, and woodinine," Tetrahedron Letters 32(37):4875-4878.
Miller et al., 2010, "Substituted tetrahydro-β-carbolines as potential agents for the treatment of human papillomavirus infection," Bioorg. Med. Chem. Lett. 20:256-259.
Saiga et al., 1987, "Synthesis of 1,2,3,4-tetrahydro-beta-carboline derivatives as hepatoprotective agents. III. Introduction of substituents onto methyl 1,2,3,4-tetrahydro-beta-carboline-2-carbodithioate," Chem. Pharm. Bull. 35(8)3284-3291.
Schoenenberger et al., 1986, "Fragmentation of Optically Active (1-Phenylethyl)- and (1-Napthylethyl) ureas in Refluxing Alcohols: Easy Preparation of Optically Active Amines of High Optical Purity," Helvetica Chimica Acta 69(6):1486-1497.
Siddiqui et al., 1992, "Preparation of Tetrahydroharmine Analogues—Their Antibacterial, Bronchodilator and Cytotoxic Activity and Effect on Central Nervous System," Proc. Pakistan Acad. Sci. 29(4):285-298.
Soe et al., 1995, "Asymmetric Pictet-Spengler Reaction with a Chiral N-(β-3-indolyl)-ethyl-1-methylbenzylamine," Tetrahedron Letters 36(11):1857-1860.
Tsuji et al., 2002, "Pictet-Spengler Reaction of Nitrones and Imines Catalyzed by Yb(OTf)3-TMSCI," Chem. Lett. 4:428-429.
Yamada et al., 1998, "Chiral Lewis Acid-Mediated Enantioselective Pictet-Spengler Reaction of Nb-Hydroxytriptamine with Aldehydes," J. Org. Chem. 63(18):6348-6354.
Donovan, 2009, "Anhydrous ethanol vs hydrous ethanol in gasoline blending," Field to Pump (available at fieldtopump.wordpress.com/2009/04/22.).
Liu et al., 2002, "Enantiomeric composition of abused amine drugs: chromatographic methods of analysis and data interpretation", J. Biochem. Biophys. Methods, 54:115-146.
Borman, 2001, "Asymmetric catalis wins", Chemical and Engineering News 79(42):5.
Laboratory Grade Ethanol, Carolina.com, Apr. 23, 2015 (available at www.carolina.com/specialty-chemicals-d-l/ethanol-laboratory-grade/FAM_861261.pr).
Lu and Rustum, "Effect of Trace Amounts of Water in the Mobile Phase of Normal-Phase Enantioselective High-Performance Liquid Chromatography on Selectivity and Resolution of Optical Isomers", Journal of Chromatographic Science, vol. 47, Apr. 2009: 320-322.

* cited by examiner

PROCESSES FOR THE PREPARATION OF SUBSTITUTED TETRAHYDRO BETA-CARBOLINES

CROSS REFERENCE TO RELATED APPLICATIONS

This application is a divisional of U.S. patent application Ser. No. 16/235,068, filed Dec. 28, 2018, which is a continuation of U.S. patent application Ser. No. 13/321,262, filed Feb. 6, 2012, which is a U.S. National Stage filing under 35 U.S.C. § 371 of International Application No. PCT/US2010/036273, filed May 27, 2010, which claims the benefit of priority to U.S. Provisional Patent Application No. 61/181,652, filed May 27, 2009, all of which are incorporated herein by reference in their entirety and for all purposes.

1. FIELD

Provided herein are processes for the synthesis of substituted tetrahydro beta-carboline derivatives. In particular, provided herein are processes useful for the preparation of (S)-4-chlorophenyl 6-chloro-1-(4-methoxyphenyl)-3,4-dihydro-1H-pyrido[3,4-b]indole-2(9H)-carboxylate.

2. BACKGROUND

Substituted tetrahydro beta-carboline derivatives have been shown to have biological activity. See International Publication Nos. WO2005/089764, WO2006/113703, WO2008/127715 and WO2008/127714, each incorporated by reference herein in their entirety.

Methods for synthesizing substituted tetrahydro beta-carboline derivatives are described in International Patent Applications Nos. WO2005/089764 and WO2006/113703. While these methods disclose various methods for preparing substituted tetrahydro beta-carboline derivatives, alternative or improved methods for their preparation, particularly for large scale, environmentally-friendly manufacturing, are still needed.

Citation of any reference in this application is not to be construed as an admission that such reference is prior art to the present application.

3. SUMMARY OF THE INVENTION

Provided herein are processes for the synthesis of substituted tetrahydro beta-carboline derivatives. Substituted tetrahydro beta-carboline derivatives have demonstrated certain therapeutic value in the inhibition of VEGF production. See International Patent Applications Nos. WO2005/089764, WO2006/113703, WO2008/127715 and WO2008/127714.

Provided herein is a process for preparing a compound of Formula (II):

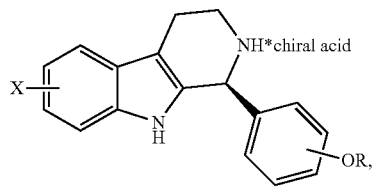

comprising the steps of
i) reacting a compound of Formula (IV) with a mixture of a chiral acid in a first solvent mixture:

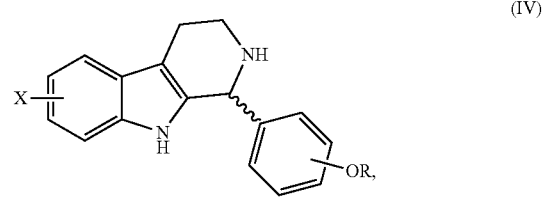

and
ii) recrystallizing the reaction product in a second solvent mixture to provide the compound of Formula (II), wherein
X is halogen; and
R is substituted or unsubstituted $C_1$ to $C_8$ alkyl.

Further provided herein is a process for preparing a compound of Formula (II):

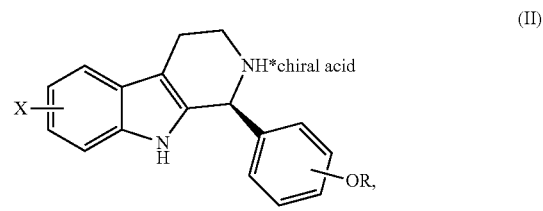

comprising the step of reacting about one equivalent of a compound of Formula (IV) with about 0.5 equivalents of a chiral acid in a first solvent mixture comprising water and a solvent in a ratio in a range of from about 1 to about 5% volume/volume water:solvent:

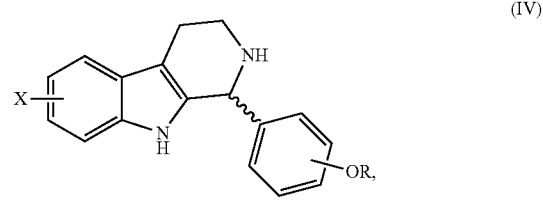

to provide the compound of Formula (II), wherein
X is halogen; and
R is substituted or unsubstituted $C_1$ to $C_8$ alkyl.

Further provided herein is a process for preparing a compound of Formula (I) or a pharmaceutically acceptable salt, hydrate or solvate thereof:

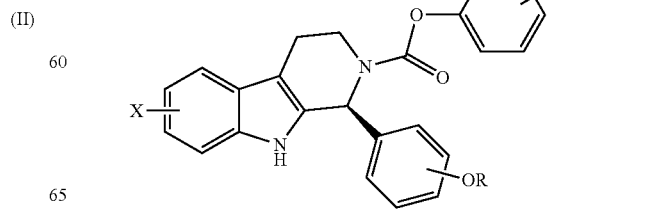

comprising the steps of:
i) reacting a compound of Formula (IV) with a chiral acid in a first solvent mixture:

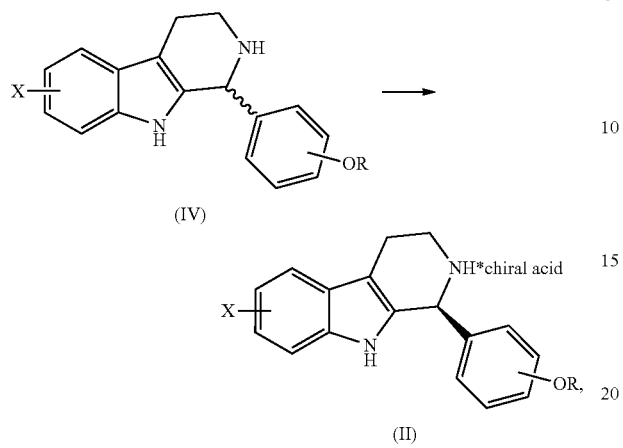

(IV)

(II)

to provide a compound of Formula (II), wherein
X is halogen; and
R is substituted or unsubstituted $C_1$ to $C_8$ alkyl; and
ii) reacting the compound of Formula (II) with a compound of Formula (III) in the presence of a base and a second solvent mixture comprising water and a solvent:

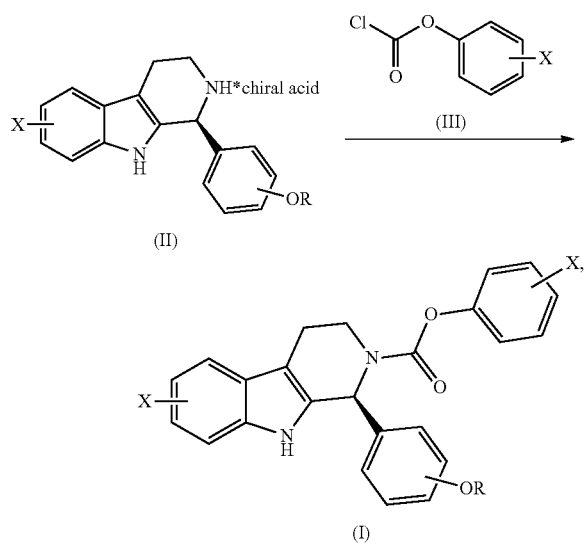

(II) (III)

(I)

to provide a compound of Formula (I), wherein
X is at each occurrence independently halogen; and
R is substituted or unsubstituted $C_1$ to $C_8$ alkyl.

In one embodiment, the first solvent mixture is a mixture of water and a solvent in a ratio in a range of from about 1 to about 5% volume/volume water:solvent.

In one embodiment, the ratio of the first solvent mixture is in a range of from about 2 to about 5% volume/volume water:solvent.

In another embodiment, the solvent in the first solvent mixture is a $C_1$-$C_8$ saturated alcohol or a mixture thereof.

In another embodiment, the solvent in the first solvent mixture is methanol, ethanol, 1-propanol, 1-butanol or a mixture thereof.

In another embodiment, the solvent in the first solvent mixture is methanol, ethanol or a mixture thereof.

In another embodiment, the solvent in the first solvent mixture is ethanol.

In one embodiment, the solvent in the second solvent mixture is iPrOAc, EtOAc, MTBE, MEK, DCM, DCE, toluene, DMA or a mixture thereof.

In another embodiment, the solvent in the second solvent mixture is EtOAc or MEK or a mixture thereof.

In another embodiment, the solvent in the second solvent mixture is MEK.

In one embodiment the compound of Formula (I) is a compound of Formula (X):

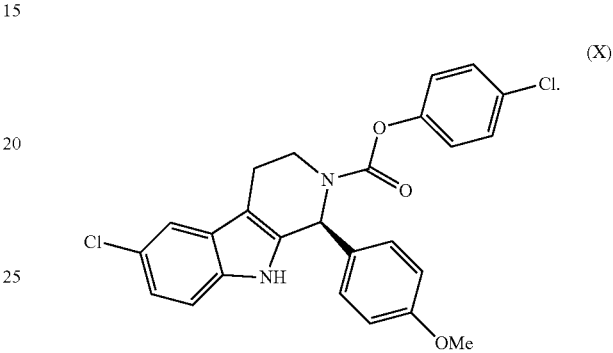

(X)

4. DETAILED DESCRIPTION OF THE INVENTION

4.1 Terminology

As used herein the terms "halogen", and "halo" refer to substituents independently selected from fluorine, chlorine, bromine, and iodine.

As used herein, the term "alkyl" generally refers to saturated hydrocarbyl radicals of straight or branched chain configuration including, but not limited to methyl, ethyl, n-propyl, isopropyl, n-butyl, isobutyl, sec-butyl, tert-butyl, n-pentyl, n-hexyl, n-heptyl, octyl, n-octyl, and the like. In some embodiments, the term "alkyl" includes $C_1$ to $C_8$, $C_1$ to $C_6$, or $C_1$ to $C_4$ alkyl.

Examples of suitable alkyl substituents include, hydrogen; or one or more substituents selected from halogen, hydroxyl, $C_1$ to $C_8$alkoxy, $C_2$ to $C_8$ alkylene; —C(O)—$R_n$; —C(O)O—$R_b$; —C(O)—NH—$R_b$; $C_3$-$C_{14}$cycloalkyl; aryl; heteroaryl; heterocyclyl; $C_1$ to $C_8$ alkyl optionally substituted with one or more substituents independently selected from hydroxyl, halogen, $C_1$ to $C_4$ alkoxy, amino, alkylamino, acetamide, —C(O)—$R_b$, —C(O)O—$R_b$, aryl, 3 to 12 membered heterocycle, or 5 to 12 membered heteroaryl, further wherein the alkylamino is optionally substituted with hydroxyl, $C_1$ to $C_4$ alkoxy, or 5 to 12 membered heteroaryl optionally substituted with $C_1$ to $C_4$ alkyl, further wherein the acetamide is optionally substituted with $C_1$ to $C_4$ alkoxy, sulfonyl, or alkylsulfonyl, further wherein the 3 to 12 membered heterocycle is optionally substituted with $C_1$ to $C_4$ alkyl optionally substituted with hydroxyl, —C(O)—$R_n$, —C(O)O—$R_n$, or oxo, further wherein the amino is optionally substituted with $C_1$ to $C_4$ alkoxycarbonyl, imidazole, isothiazole, pyrazole, pyridine, pyrazine, pyrimidine, pyrrole, thiazole or sulfonyl substituted with $C_1$ to $C_6$ alkyl, wherein pyridine and thiazole are each optionally substituted with $C_1$ to $C_4$ alkyl;

wherein, $R_b$ is hydroxyl; amino; alkylamino optionally substituted with hydroxyl, amino, alkylamino, $C_1$ to $C_4$ alkoxy, 3 to 12 membered heterocycle optionally substituted with one or more independently selected $C_1$ to $C_6$ alkyl, oxo, —C(O)O—$R_n$, or 5 to 12 membered heteroaryl optionally substituted with $C_1$ to $C_4$ alkyl; $C_1$ to $C_4$ alkoxy; $C_2$ to $C_8$ alkenyl; $C_2$ to $C_8$ alkynyl; aryl, wherein the aryl is optionally substituted with one or more substituents independently selected from halogen or $C_1$ to $C_4$ alkoxy; 5 to 12 membered heteroaryl; 3 to 12 membered heterocycle optionally substituted with one or more substituents independently selected from acetamide, —C(O)O—$R_n$, 5 to 6 membered heterocycle, or $C_1$ to $C_6$ alkyl optionally substituted with hydroxyl, $C_1$ to $C_4$ alkoxy, amino, or alkylamino; or $C_1$ to $C_8$ alkyl optionally substituted with one or more substituents independently selected from $C_1$ to $C_4$ alkoxy, aryl, amino, or 3 to 12 membered heterocycle, wherein the amino and 3 to 12 membered heterocycle are optionally substituted with one or more substituents independently selected from $C_1$ to $C_6$ alkyl, oxo, or —C(O)O—$R_n$; and wherein, $R_n$ is hydroxyl, $C_1$ to $C_4$ alkoxy, amino, or $C_1$ to $C_6$ alkyl.

As used herein and unless otherwise indicated, the term "process(es) of preparing" or "process(es) for the preparation" refers to the methods disclosed herein which are useful for preparing a compound disclosed herein. Modifications to the methods disclosed herein (e.g., starting materials, reagents, protecting groups, solvents, temperatures, reaction times, purification) are also encompassed by the methods and processes provided herein.

As used herein and unless otherwise indicated, the term "adding", "reacting" or "in the presence of" and the like means contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order, unless otherwise specified. They can be added in the presence or absence of heat and can optionally be added under an inert atmosphere. "Reacting" can refer to in situ formation or intramolecular reaction where the reactive groups are in the same molecule.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Compounds provided herein include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Others are well-known in the art, see for example, *Remington's Pharmaceutical Sciences*, 18th eds., Mack Publishing, Easton Pa. (1990) or *Remington: The Science and Practice of Pharmacy*, 19 th eds., Mack Publishing, Easton Pa. (1995).

As used herein, "about" means a range around a given value wherein the resulting process is substantially the same as a process with the recited value. In one embodiment, "about" means within 25% of a given value or range. For example, "70% by weight" of a compound present in a composition comprises at least all compositions in which the component is present from 52% to 88% by weight. In another embodiment "about" means within 10% of a given value or range. For example, 70% by weight of a component present in a composition comprises at least all compositions in which the component is present from 63% to 77% by weight.

Acronyms or symbols for groups or reagents have the following definitions: AUC=area under the curve; DCE=dichloroethene, DCM=dichloromethane, DMA=dimethylacetamide EtOAc=ethyl acetate; HPLC=high performance liquid chromatography; IPC=In-process control/check; iPrOAc=isopropyl acetate, MEK=methyl ethyl ketone, MTBE=methyl tert-butyl ether, VEGF=vascular endothelial growth factor.

4.2 Processes

In one embodiment provided herein is a process for the preparation of substituted tetrahydro beta-carboline derivatives of Formula (I):

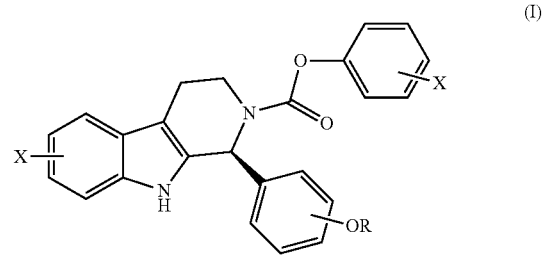

or a pharmaceutically acceptable salt, hydrate or solvate thereof, wherein X is at each occurrence independently halogen; and R is substituted or unsubstituted $C_1$ to $C_8$ alkyl.

In one embodiment, the tetrahydro beta-carboline is a compound of Formula (Ia):

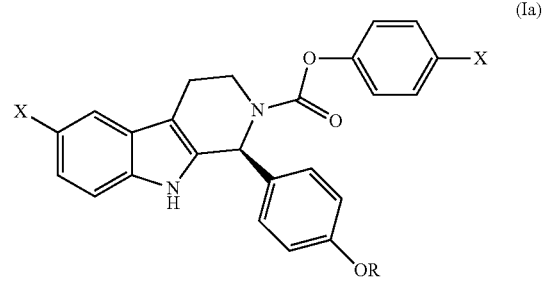

or a pharmaceutically acceptable salt, hydrate or solvate thereof, wherein X is at each occurrence independently halogen; and R is substituted or unsubstituted $C_1$ to $C_8$ alkyl.

In one embodiment, the tetrahydro beta-carboline is a compound of Formula (I) or (Ia) or a pharmaceutically acceptable salt, hydrate or solvate thereof, wherein X is Cl.

In another embodiment the tetrahydro beta-carboline is a compound of Formula (I) or (Ia) or a pharmaceutically acceptable salt, hydrate or solvate thereof, wherein R is methyl.

In a specific embodiment the tetrahydro beta-carboline is a compound of Formula (I) or (Ia) or a pharmaceutically acceptable salt, hydrate or solvate thereof, wherein X is Cl and R is methyl.

In one embodiment the tetrahydro beta-carboline is (S)-4-chlorophenyl 6-chloro-1-(4-methoxyphenyl)-3,4-dihydro-1H-pyrido[3,4-b]indole-2(9H)-carboxylate, having the structure of Formula (X):

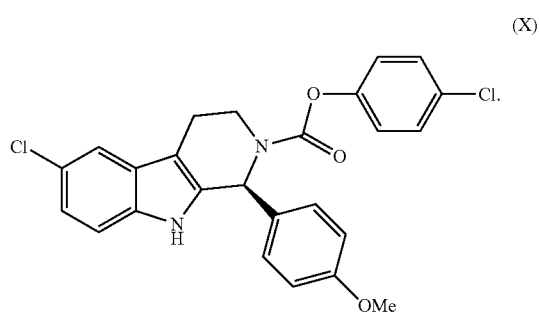 [SMILES: COc1ccc([C@H]2c3[nH]c4ccc(Cl)cc4c3CCN2C(=O)Oc2ccc(Cl)cc2)cc1]

(X)

In one embodiment provided herein is a process for preparing a compound of Formula (I) or a pharmaceutically acceptable salt, hydrate or solvate thereof, wherein X is at each occurrence independently halogen; and R is substituted or unsubstituted $C_1$ to $C_8$ alkyl, comprising the step of reacting a compound of Formula (II) with a compound of Formula (III) as shown in Scheme A.

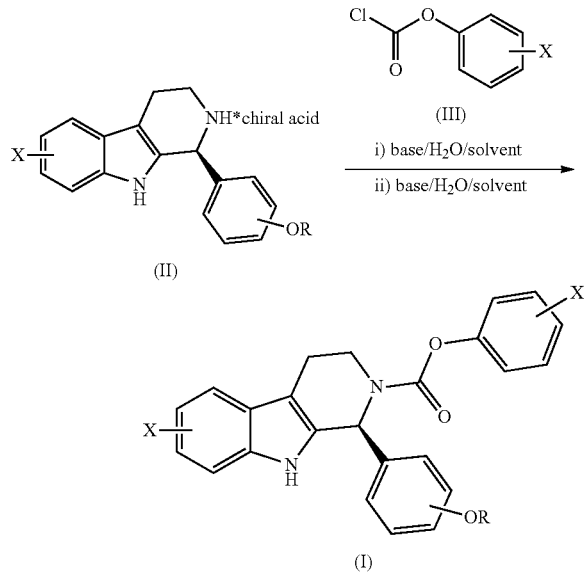

In a first step (i), a compound of Formula (II), such as (S)-6-chloro-1-(4-methoxyphenyl)-2,3,4,9-tetrahydro-1H-pyrido[3,4-b]indole (S)-2-acetamido-3-phenylpropanoate, is converted to the free base by dissolving a compound of Formula (II) in a second solvent mixture comprising water and a suitable organic solvent, such as iPrOAc, EtOAc, MTBE, MEK, DCM, DCE, toluene, DMA or a mixture thereof, and adding a first portion of a suitable base, such as an aqueous potassium carbonate solution. The biphasic mixture is stirred at a suitable temperature, such as a range of from about 20 to about 40° C. for a suitable time, such as a range of from about 1 to about 4 h, then the aqueous phase is removed, and the organic layer is washed with water until a suitable pH, such as less than about pH 7.5 is reached. The solvent volume is reduced, e.g., to about 50% of the original solvent volume, by a suitable method, such as by distillation with or without vacuum at a suitable temperature, such as less than about 30° C.

In an embodiment of the first step (i), the suitable solvent is EtOAc or MEK or a mixture thereof.

In an embodiment of the first step (i), the suitable solvent is MEK.

In a second step (ii), a second portion of a suitable base is added, such as an aqueous potassium carbonate solution, and the mixture is reacted with a compound of Formula (III), such as 4-chlorophenyl chloroformate, for a suitable time, such as a range of from about 1 to about 4 h, at a suitable temperature, such as a range of less than from about 35 to about 45° C.

In an embodiment of the second step (ii), the suitable temperature for the reaction is less than about 40-2° C.

The reaction mixture from the second step (ii) is cooled to a suitable temperature, such as a range of from about 20 to about 30° C., then the aqueous phase is removed. The organic layer is washed with water until a suitable pH, such as less than about pH 7.5 is reached. The organic solution is filtered via an in-line filter such as PE or PP filter. The volume of the second solvent mixture is reduced, e.g., to about 20% of the original solvent volume, by a suitable method, such as by distillation with or without vacuum at a suitable temperature, such as less than about 50° C. The remaining mixture is cooled to a suitable temperature, such as a range of from about 20 to about 30° C. for a suitable time, such as a range of from about 1 to about 4 h, then heptanes are added over a suitable time, such as a range of from about 1 to about 4 h. The mixture is stirred for a suitable time, such as a range of from about 1 to about 4 h at a suitable temperature, such as a range of from about 20 to about 30° C.

In an embodiment of the second step (ii), the suitable temperature to which the reaction mixture is cooled is about 25±3° C., the suitable temperature to which the distillation mixture is cooled is about 25±3° C. and the suitable temperature at which the heptane mixture is stirred is about 25±3° C.

The heptane mixture is filtered, washed with water and a third solvent mixture comprising a suitable solvent in a mixture with heptanes, such as a mixture of EtOAc and heptanes or a mixture of MEK and heptanes, and dried at a suitable temperature, such as a range of from about 45 to about 55° C., for a suitable time, such as about 1-3 days to give a target compound of Formula (I). The resulting material of Formula (I) can optionally be further purified. For example, a compound of Formula (I) can be taken up in a suitable solvent, such as EtOAc or MEK, in a suitable amount, such as up to about 9×, and warmed to a suitable temperature, such as a range of from about 85 to about 90° C., and stirred for a suitable time, such as a range of from about 1 to about 3 h. The mixture is then cooled to a suitable temperature, such as a range of from about 20 to about 30° C. for a suitable time, such as a range of from about 1 to about 4 h, and heptanes are added over a suitable time, such as a range of from about 1 to about 4 h. The mixture can then be filtered, washed with the third solvent mixture, and dried to give a purified compound of Formula (I).

In one embodiment of the second step (ii), the suitable temperature to which the Formula (I) mixture is cooled is about 25-3° C.

In another embodiment, the third solvent mixture is a mixture of MEK and heptanes.

In another embodiment, the solvent in the Formula (I) mixture is MEK.

In one embodiment provided herein is a process for preparing a compound of Formula (II), wherein X is halogen; and R is substituted or unsubstituted $C_1$ to $C_8$ alkyl, comprising the step of reacting a compound of Formula (IV) with a chiral acid as shown in Scheme B.

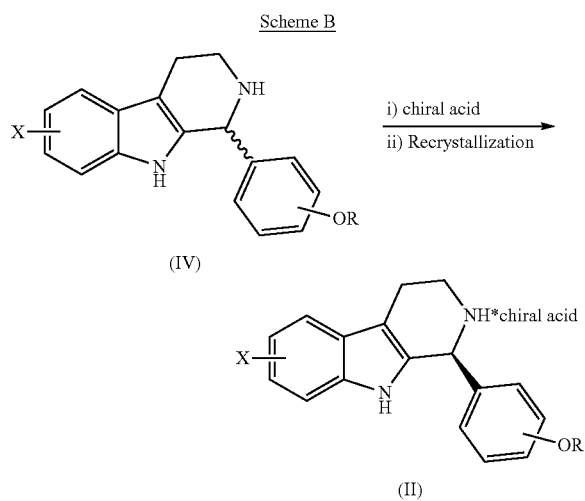

Scheme B (IV)

(II)

In a first step (i), the chiral resolution step, a compound of Formula (IV) is reacted with a suitable chiral acid, in a first solvent mixture comprising water and a suitable solvent, at a suitable temperature, such as about 64° C. or about 78° C., for a suitable time, such as about 15-45 min. The reaction mixture is then cooled to a suitable temperature, such as about 20-30° C. over a suitable time, such as 2-4 h, then stirred for a suitable time, such as about 10-20 h, at a suitable temperature, such as about 20-30° C.

The reaction mixture is filtered and in a second step (ii), the recrystallization step, a suitable solvent, such as ethanol, is added and the recrystallization mixture is heated to a suitable temperature, such as about 78° C. for a suitable time. The recrystallization mixture is then cooled to a suitable temperature, such as about 20-30° C., over a suitable time, such as 2-4 h, stirred for a suitable time, such as about 10-20 h, at a suitable temperature, such as about 20-30° C., filtered and dried at a suitable temperature, such as about 45-55° C. for a suitable time, such as about 1-3 days to give a compound of Formula (II).

In one embodiment, the first solvent mixture comprising water and a solvent are in a ratio in a range of from about 1 to about 5% volume/volume water:solvent.

In another embodiment, the ratio of the first solvent mixture is in a range of from about 2 to about 5% volume/volume water:solvent.

In another embodiment, the solvent in the first solvent mixture is methanol, ethanol, 1-propanol, 1-butanol or a mixture thereof.

In another embodiment, the solvent in the first solvent mixture is methanol, ethanol or a mixture thereof.

In another embodiment, the solvent in the first solvent mixture is ethanol.

In an alternative embodiment, the process shown in Scheme B is carried out as a seeded chiral resolution process.

In a first step (i) of the seeded chiral resolution process, the chiral resolution step, about one equivalent of a compound of Formula (IV) is reacted with a suitable chiral acid in a range of from about 0.1 to about 0.5 equivalents, in a first solvent mixture comprising water and a suitable solvent, such as methanol, ethanol, 1-propanol, or 1-butanol or a mixture thereof in a ratio in a range of from about 1 to about 5% v/v (volume/volume) of water:solvent. The resolution mixture was treated with a suitable seed of Formula (IV), such as an amount in a range of from about 1 to about 2% by weight of Formula (IV) at a suitable temperature, such as about a range of from about 50 to about 60° C. The mixture is then cooled to a suitable temperature, such as a range of from about 10 to about 20° C. over a suitable time, such as a range of from about 1 to about 2 h, then stirred for a suitable time, such as a range of from about 1 to about 2 h, at a suitable temperature, such as a range of from about 10 to about 20° C.

In one embodiment, the ratio of the first solvent mixture is in a range of from about 2 to about 5% volume/volume water:solvent.

In another embodiment, the solvent in the first solvent mixture is methanol, ethanol or a mixture thereof.

In another embodiment, the solvent in the first solvent mixture is ethanol.

In another embodiment, the solvent in the first solvent mixture is ethanol.

In an embodiment of the first step (i), the suitable seeding temperature is about 55±3° C., the suitable temperature to which the seeded mixture is cooled is about 15-2° C. and the suitable temperature at which the cooled mixture is stirred is about 15±2° C.

The cooled mixture is then filtered and in a second step (ii), the slurry wash step, the first solvent mixture is added and the mixture is stirred to a suitable temperature, such as a range of from about 20 to about 25° C. for a suitable time. The suspension is then cooled to a suitable temperature, such as a range of from about 10 to about 20° C., over a suitable time, filtered and dried at a suitable temperature, such as a range of from about 45 to about 55° C. for a suitable time, such as about 1-3 days to give a compound of Formula (II).

In an embodiment of the second slurry wash step (i), the suitable temperature at which the mixture is stirred is about 22±2° C. and the suitable temperature to which the suspension is cooled is about 15±2° C.

In a certain embodiment, the process shown in Scheme B1 is carried out as a one step procedure for preparing a compound of Formula (II), without the recrystallization step.

Scheme B1

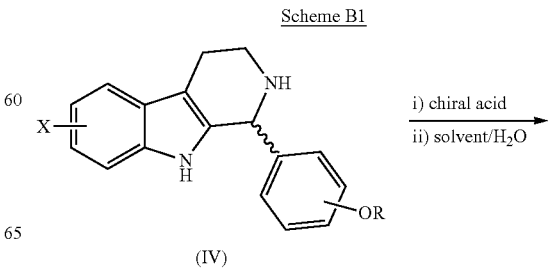

(IV)

-continued

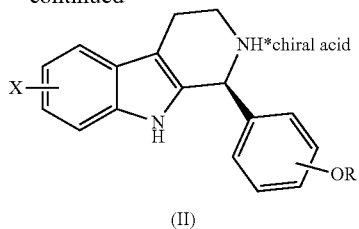

(II)

A compound of Formula (IV) (1 eq.) is reacted with a suitable chiral acid (in an amount of about 0.51 equivalents), in a first solvent mixture, for a suitable time, such as about 16-20 h. Upon cooling, filtration and drying, a compound of Formula (II) is obtained. In one embodiment, the first solvent mixture is a mixture of ethanol and water in a ratio in a range of from about 1 to about 5% v/v (volume/volume) of water:ethanol. In another embodiment, the first solvent mixture is a mixture of ethanol and water in a ratio in a range of from about 2 to about 5% v/v (volume/volume) of water:ethanol. In certain embodiments the enantiomeric excess is greater than about 90% e.e. In certain embodiments, the enantiomeric excess is greater than about 95% e.e. In certain embodiments, the enantiomeric excess is greater than about 98% e.e. In certain embodiments, the enantiomeric excess is greater than about 99% e.e. In certain embodiments, the enantiomeric excess is greater than about 99.5% e.e. In certain embodiments, the enantiomeric excess is about 100% e.e.

In another embodiment, one equivalent of a compound of Formula (IV) is reacted with about 0.5, about 0.8, or about 0.5 to about 1.0 equivalents of a suitable chiral acid. Embodiments of the chiral acid include, and are not limited to, N-acetyl-L-phenylalanine (also referred to as (S)-2-acetamido-3-phenylpropanoic acid), (S)-2-(methoxycarbonylamino)-3-phenylpropanoic acid, (S)-2-(isopropoxycarbonylamino)-3-phenylpropanoic acid, (S)-2-benzamido-3-phenylpropanoic acid, (S)-2-(4-chlorobenzamido)-3-phenylpropanoic acid, (S)-2-(4-methoxybenzamido)-3-phenylpropanoic acid, (S)-3-phenyl-2-(4-(trifluoromethyl)benzamido)propanoic acid, (S)-2-isobutyramido-3-phenylpropanoic acid, (S)-3-phenyl-2-(phenylsulfonamido)propanoic acid, (S)-3-phenyl-2-(4-(trifluoromethyl)phenylsulfonamido)propanoic acid, (S)-2-(4-methoxyphenylsulfonamido)-3-phenylpropanoic acid, (S)-2-(4-methylphenylsulfonamido)-3-phenylpropanoic acid, (1,1'-binaphtalene)-2,2'-dicarboxylic acid, 3-bromo-8-camphorsulfonic acid, camphor-8-sulfonic acid, camphor-10-sulfonic acid, 2,3:4,6-di-O-isopropylidene-xylo-hexulosonic acid, 4-hydroxydinaphtho[2,1-d:'1,2'-f]-1,3,2-dioxaphoshpepin 4-oxide, 4-hydroxy-3-phenylbutanoic acid lactone, Mosher's acid, lactic acid and its derivatives, mandelic acid and its derivatives, 3-menthoxyacetic acid, 3-menthylglycine, 2-methyl-2-phenylbutanedioic acid, naproxen, 5-oxo-2-pyrrolidinescarboxylic acids, 2-[((phenylamino)carbonyl)oxy]propanoic acid, 1-phenylethanesulfonic acid, tartaric acid and its derivatives, 1,2,3,4-tetrahydro-3-isoquinoline sulfonic acid (2,4,5,7-tetranitro-9-fuorenylideneaminoxy)-propionic acid, 4-thiazolidenecarboxylic acid and further reagents disclosed in CRC Handbook of Optical Resolutions via Diastereomeric Salt Formation, D. Kozma (Editor), CRC Press 2002, pages 51-61 and Appendix 2 (pages 579-625), herewith incorporated by reference in its entirety.

In another embodiment, the chiral acid is N-acetyl-L-phenylalanine, (S)-2-(methoxycarbonylamino)-3-phenylpropanoic acid, (S)-2-(isopropoxycarbonylamino)-3-phenylpropanoic acid, (S)-2-benzamido-3-phenylpropanoic acid, (S)-2-(4-chlorobenzamido)-3-phenylpropanoic acid, (S)-2-(4-methoxybenzamido)-3-phenylpropanoic acid, (S)-3-phenyl-2-(4-(trifluoromethyl)benzamido)propanoic acid, (S)-2-isobutyramido-3-phenylpropanoic acid, (S)-3-phenyl-2-(phenylsulfonamido)propanoic acid, (S)-3-phenyl-2-(4-(trifluoromethyl)phenylsulfonamido)propanoic acid, (S)-2-(4-methoxyphenylsulfonamido)-3-phenylpropanoic acid or (S)-2-(4-methylphenylsulfonamido)-3-phenylpropanoic acid.

In another embodiment, the chiral acid is N-acetyl-L-phenylalanine.

In one embodiment provided herein is a process for preparing a compound of Formula (IV), wherein X is halogen; and R is substituted or unsubstituted $C_1$ to $C_8$ alkyl, comprising the step of reacting a compound of Formula (V), wherein HB is an acid suitable to form a salt with a compound of Formula (V), such as hydrochloric acid or acetic acid, with a solvated base as shown in Scheme C.

Scheme C

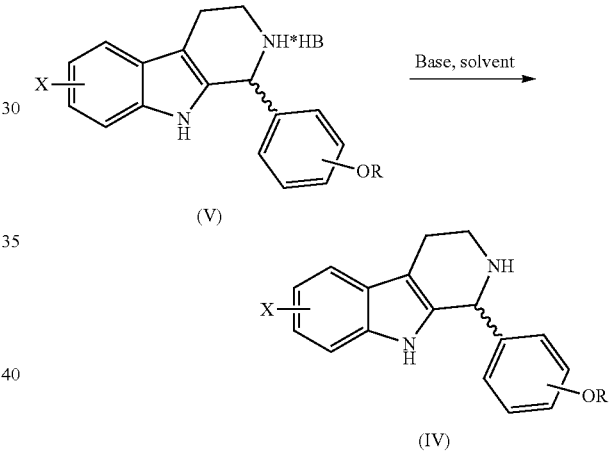

A compound of Formula (V), in a suitable solvent, such as water, is mixed with a suitable base, such as aqueous ammonium hydroxide, and a suitable solvent, such as EtOAc or iPrOAc. The resulting mixture is heated to a suitable temperature, such as about 25-35° C., for a suitable time, such as about 15-45 min, and then cooled to a suitable temperature, such as about 20-30° C., and agitated for a suitable time, such as about 30-90 min. The aqueous phase is removed and the organic layer is washed with water. The volume of the organic layer is reduced under vacuum to a suitable extent, such as about 20% of the original organic solvent volume, by heating to a suitable temperature, such as not more than about 50° C. The remaining volume is charged with a suitable solvent, such as heptane or heptanes, stirred for a suitable time, such as about 1-3 h, at a suitable temperature, such as about 20-30° C., and the compound of Formula (IV) is isolated by filtration and dried at a suitable temperature, such as about 45-55° C., for a suitable time, such as 1-3 days.

In one embodiment provided herein is a process of preparing a compound of Formula (V), wherein X is halogen; R is substituted or unsubstituted $C_1$ to $C_8$ alkyl; wherein HB is an acid suitable to form a salt with a compound of Formula (V), comprising the step of reacting a compound of Formula (VII) in the presence of an acid HB and a solvent, wherein HB' is an acid suitable to form a salt with the amino group of a compound of Formula (VII), with a compound of Formula (VI) as shown in Scheme D.

Scheme D

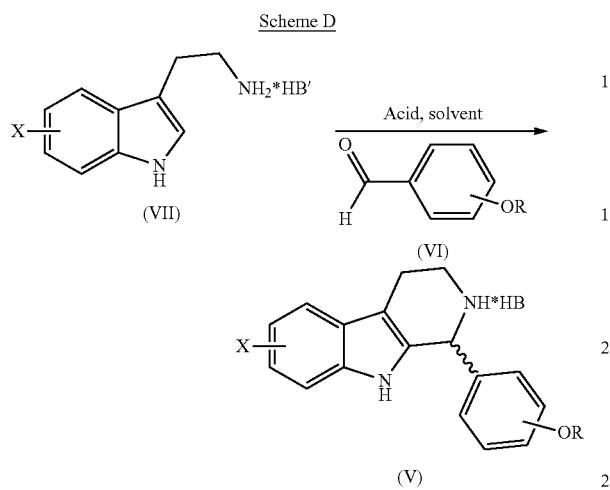

A compound of Formula (VII), such as a substituted 5-chlorotryptamine hydrochloride salt is reacted with a compound of Formula (VI), such as an alkyl substituted aldehyde compound of Formula (VI), in the presence of a first suitable acid, such as hydrochloric acid, in a suitable solvent, such as water or EtOAc, at a suitable concentration, such as about 0.3-0.7M, at a suitable temperature, such as about 100° C., for a suitable time, such as about 10-20 h. The mixture is cooled to a suitable temperature, such as about 20-30° C., and filtered. The obtained crude solid is stirred with a second suitable acid, such as acetic acid for a suitable time, such as about 30-90 min, at a suitable temperature, such as about 20-30° C., then filtered and washed with a suitable acid, such as acetic acid. The crude product is stirred in the suitable solvent, such as water or EtOAc, for a suitable time, such as about 0.5-2 h, at a suitable temperature, such as about 20-30° C., then filtered and washed with the suitable solvent, such as water or EtOAc to provide a target compound of Formula (V). The compound of Formula (V) is dried for a suitable time, such as a range of from about 1 to about 6 days under vacuum at a suitable temperature, such as about 45-55° C.

In certain embodiments, the first suitable solvent is water.

In certain embodiments, the processes provided herein comprise multiple steps, as described above.

In one embodiment provided herein is a process for the preparation of substituted tetrahydro beta-carboline derivatives of Formula (I):

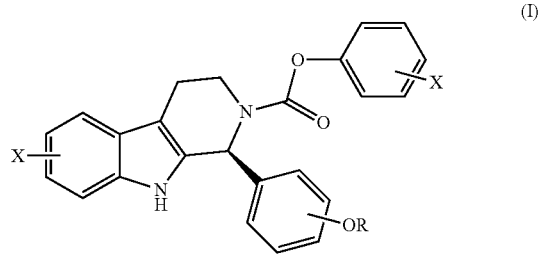

(I)

or a pharmaceutically acceptable salt, hydrate or solvate thereof, wherein X is at each occurrence independently halogen; and R is substituted or unsubstituted $C_1$ to $C_8$ alkyl;

comprising the step of reacting a compound of Formula (VII), wherein HB' is an acid suitable to form a salt with the amino group of a compound of Formula (VII) such as hydrochloric acid or acetic acid, with an aldehyde compound of Formula (VI) in the presence of a suitable acid, such as hydrochloric acid, and a solvent, such as water or EtOAc, to provide a compound of Formula (V):

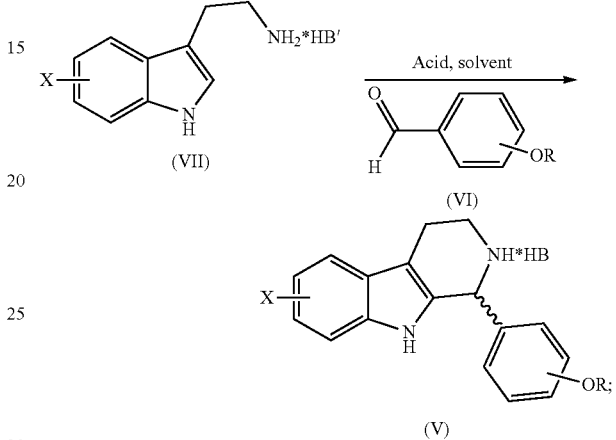

further comprising the step of reacting a compound of Formula (V), wherein HB is an acid suitable to form a salt with a compound of Formula (V) such as hydrochloric acid or acetic acid, with a base, such as $NH_4OH$ in the presence of a solvent to provide a compound of Formula (IV):

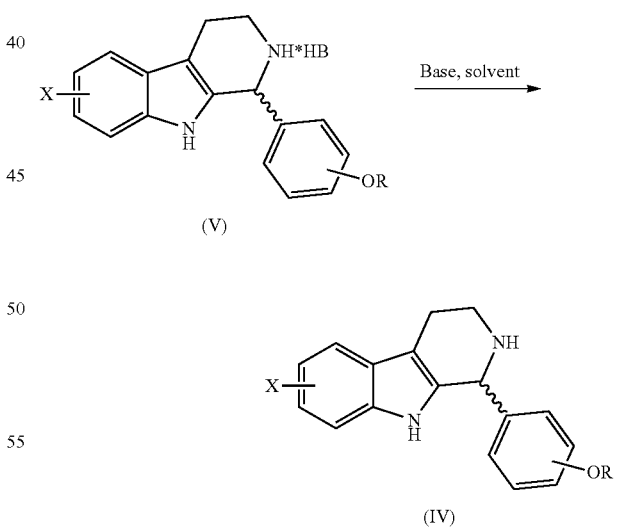

further comprising the step of reacting a compound of Formula (IV) with a chiral acid, in a first solvent mixture comprising a ratio of water:solvent, wherein the solvent is methanol, ethanol or a mixture thereof, then optionally recrystallizing the reaction product in a second solvent mixture comprising water and a solvent, wherein the solvent is ethanol to provide a compound of Formula (II):

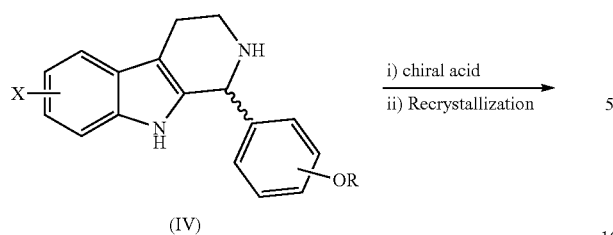

(IV)

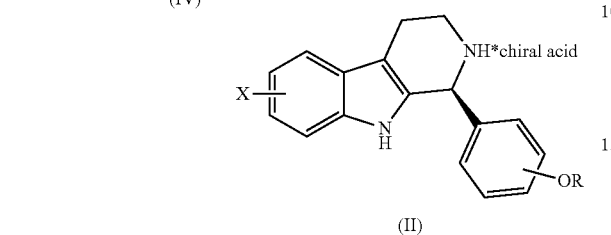

(II)

further comprising the step of reacting a compound of Formula (II) with a compound of Formula (III) to provide the compound of Formula (I):

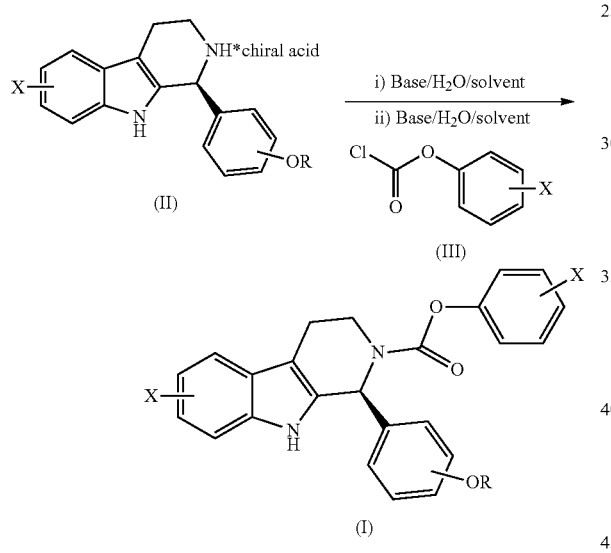

further comprising the step of optionally purifying a compound of Formula (I), by taking up a compound of Formula (I) in a suitable solvent, such as MEK or EtOAc, in a suitable amount, such as up to about 9×, then warming, stirring, filtering, and washing with a suitable solvent mixture, such as a mixture of EtOAc and heptanes or a mixture of MEK and heptanes, and drying; wherein, in one embodiment, the suitable solvent mixture is a mixture of MEK and heptanes;

wherein, for a compound of Formula (I), each occurrence of X is independently halogen, in one embodiment chloro, and R is substituted or unsubstituted $C_1$ to $C_8$ alkyl; and, wherein, in one embodiment, alkyl is methyl.

The embodiments described herein are further illustrated by the examples set forth in Section 5 below, which are not to be construed as limiting the scope of the embodiments described herein.

Starting materials and reagents useful in the processes described herein can be obtained from commercial sources or prepared using methods known to one skilled in the art.

5. EXAMPLES

5.1 Synthesis of (5)-4-chlorophenyl 6-chloro-1-(4-methoxyphenyl)-3,4-dihydro-1H-pyrido[3,4-b]indole-2(9H)-carboxylate, compound of Formula (X)

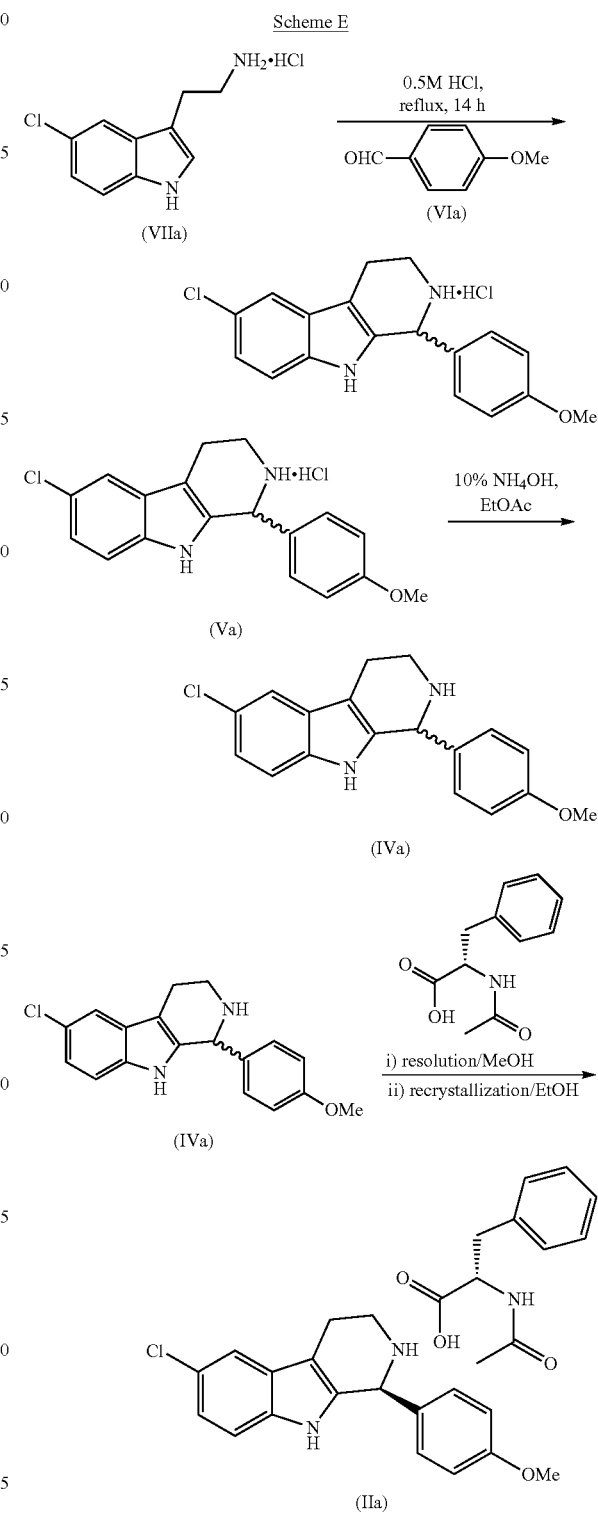

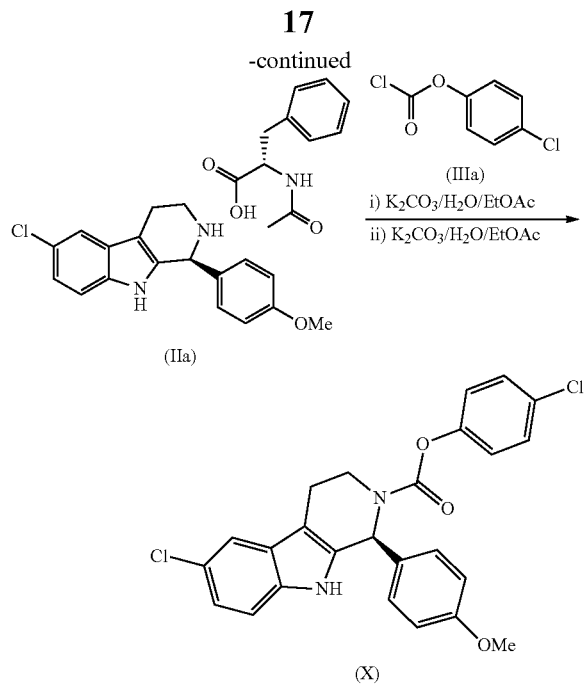

5.1.1 Synthesis of 6-chloro-1-(4-methoxyphenyl)-2,3,4,9-tetrahydro-1H-pyrido[3,4-b]indole hydrochloride, Compound of Formula (Va)

General Information.

The reaction depicted in Scheme E was performed in a 300-gallon glass-lined reactor. A 5-Chlorotryptamine*HC compound of Formula (VIIa) was purchased from ABChem Technologies (99% AUC) and a p-anisaldehyde compound of Formula (VIa) was purchased from Alfa Aesar (99.7% AUC). Reagent grades of 37% HCl, acetic acid and ethyl acetate were used.

Procedure.

A solution of 0.5M HCl was prepared by diluting 37% HCl (16.9 Kg) in purified water (329.0 Kg). 5-Chlorotryptamine hydrochloride salt compound of Formula (VIIa) (40.0 Kg, 173.1 mol, 1.0 eq) was charged into the reactor followed by the 0.5M HCl (340.6 Kg, 8.5×) and p-anisaldehyde compound of Formula (Via) (28.5 Kg, 209.3 mol, 1.2 eq). The resulting slurry was warmed to 100±2° C. and refluxed for 14 hours. The slurry was cooled to <45° C. and sampled by HPLC analysis for IPC (Limit: ≤1.0% of the 5-chlorotryptamine hydrochloride salt compound of Formula (VIIa) relative to target compound of Formula (Va)) and found to pass. The slurry was cooled to 25±2° C. and filtered on a Nutsche filter. A sample of the wet cake was taken for information purposes. The wet cake (150.1 Kg) was recharged to the vessel followed by acetic acid (181.6 Kg, 4.5×) and the slurry stirred at 25±2° C. for 1 hour. The slurry was filtered on the Nutsche filter and the cake washed with acetic acid (45.4 Kg, 1.1×). A sample of the wet cake was taken for information purposes. The wet cake (149.8 Kg) was recharged to the vessel followed by ethyl acetate (155.7 Kg, 3.9×) and the slurry stirred at 25±+2° C. for 1 hour. The slurry was filtered on the Nutsche filter and the cake washed with ethyl acetate (38.9 Kg, 1.0×). Additional ethyl acetate (20 Kg, 0.5×) was used to remove residual compound of Formula (Va) from the vessel. The wet cake (113.3 Kg) was dried at a set-point of 50° C. for 4 days under vacuum. A total of 55.1 Kg compound of Formula (Va) was obtained as an off-white solid. Mp=302° C. (dec.); IR: 3168, 2906, 2767, 1612, 1513, 1421, 1248, 1174, 1032 cm$^{-1}$; HPLC (std): 7.89 min; ES-MS=313.33 (M$^+$H); $^1$H NMR (300 MHz, DMSO-d6) δ 11.06 (s, 1H), 7.58 (s, 1H), 7.29 (dd, 3H), 6.99-7.10 (m, 3H), 5.87 (s, 1H), 3.76 (s, 3H), 3.33 (m, br, 2H), 2.94-3.13 (m, 2H).

5.1.2 Synthesis of 6-chloro-1-(4-methoxyphenyl)-2,3,4,9-tetrahydro-1H-pyrido[3,4-b]indole Compound of Formula (IVa)

General Information.

The reaction depicted in Scheme E was performed in a 300-gallon glass-lined reactor. Reagent grade ammonium hydroxide, 37% hydrochloric acid and ethyl acetate were used along with technical grade heptane. For the HCl scrubber (100 gallon reactor), potable water was used and purified water from the house system for all other processing purposes.

Procedure.

An HCl scrubber was prepared in a 100 gallon reactor by diluting 37% hydrochloric acid (182.9 Kg) with potable water (240 L). Compound of Formula (Va) (55.1 Kg, 157.8 mol) was charged into the 300-gallon reactor followed by purified water (225 L, 4.1×), 28-30% ammonium hydroxide (124.5 Kg, 138 L, 1031.6 mol, 2.5×), then ethyl acetate (497 Kg, 552 L, 10×). The mixture was heated to 30±2° C. for 30 minutes and then cooled to 25±2° C. and agitated for a further hour. The biphasic mixture was sampled for solids and pH analysis (IPC Limit: Free of visible solids, pH of aqueous phase >9.0) and found to pass. The aqueous phase was removed and the organic phase washed twice with water (2×367 L, 2×6.7×) to achieve an aqueous phase pH of <7.5. The batch was distilled under vacuum to a volume of ~2× (~110 L; maximum batch temperature: 30° C.). Heptane (376.9 Kg, 551 L, 10×) was charged over about 2 hours and agitated at 25±2° C. for a further 2 hours. The product compound of Formula (IVa) was isolated on the Nutsche filter and washed with a mixture of heptane (125.6 Kg, 183 L, 3.3×) and ethyl acetate (16.5 Kg, 18 L, 0.3×). The wet cake (67.6 Kg) was dried at a set-point of 50° C. for 2 days under vacuum. A total of 46.3 Kg compound of Formula (IVa) was obtained as an off-white solid. Mp=161° C.; IR: 2903, 2836, 1610, 1511, 1439, 1243, 1173, 1029 cm$^{-1}$; HPLC (std): 7.89 min; HPLC (chiralPAK AD-H, 20% IPA in hexane): 13.3, 18.3 min; ES-MS=313.33 (M$^+$H); $^1$H NMR (300 MHz, CDCl$_3$) δ 7.61 (s, br, 1H), 7.49 (s, 1H), 7.05-7.26 (m, 4H), 6.85-6.90 (m, 2H), 5.09 (s, 1H), 3.80 (s, 3H), 3.15-3.40 (m, 1H), 3.07-3.14 (m, 1H), 2.72-2.91 (m, 2H), 1.75 (s, 1H).

5.1.3 Alternative Synthesis of 6-chloro-1-(4-methoxyphenyl)-2,3,4,9-tetrahydro-1H-pyrido[3,4-b]indole Compound of Formula (IVa)

Procedure.

To deionized water (8 L), concentrated hydrochloric acid (0.36 L) was added slowly while maintaining the temperature between 23° C. and 17° C. The 5-Chlorotryptamine hydrochloride salt compound of Formula (VIIa) (1 kg) was charged into the reaction vessel and then the p-anisaldehyde compound of Formula (VIa) (0.60 L) was added while maintaining the temperature between 23° C. and 17° C. The suspension was heated to reflux and kept under reflux until completion of the reaction. The reaction is complete after 8-18 hours, when the content of 5-chlorotryptamine hydrochloride is NMT 1.0% as determined by percent HPLC area.

The suspension was cooled to a temperature of between about 27° C. and 23° C. The suspension was then filtered to provide a crude, wet (±)-piperidinoindole hydrochloride product.

To pure acetic acid (4 L), the crude, wet (±)-piperidinoindole hydrochloride was added. The suspension was stirred at a temperature of between about 27° C. and 23° C. for a period of at least 1 hour. The suspension was then filtered to provide a wet product that was then washed with pure acetic acid (0.5 L). The wash was repeated with pure acetic acid (0.5 L) added to the wet product. The wet (±)-piperidinoindole hydrochloride product was added to ethyl acetate (4 L) and the suspension was stirred at a temperature of between about 27° C. and 23° C. for a period of at least 1 hour. The suspension was then filtered to provide a wet (±)-piperidinoindole hydrochloride product. The wet product was washed twice with ethyl acetate (0.8 L). and then weighed to obtain the wet weight (Wwet). A sample of the wet product was also used to determine LOD for the content of residual solvents.

Calculate the weight (W) (kg) of the wet (±)-piperidinoindole hydrochloride product using the formula W=Wwet−(Wwet×LOD/100) kg.

To deionized water (4×W)L add the wet (±)-piperidinoindole hydrochloride (Wwet)kg isolated above while maintaining the temperature between 25° C. and 15° C. Add ethyl acetate (10×W)L to the solution while maintaining the temperature between 25° C. and 15° C. Over a period of 30 minutes, add 25% ammonium hydroxide (2.8×W)L while maintaining the temperature between 30° C. and 15° C. Heat the temperature of the reaction mixture to a temperature of between about 27° C. and 33° C. and stir for at least 30 minutes at a temperature of between about 27° C. and 33° C. Cool down the reaction mixture to temperature of between about 28° C. and 22° C. and stir the reaction mixture at a temperature of between about 28° C. and 22° C. for a period of at least 60 minutes. Take a sample of the reaction mixture for pH measurement of the aqueous phase. Stop stirring and allow the phases to separate for a period of at least 30 minutes. Discharge the aqueous phase, then add ethyl acetate (5×W)L to the organic phase while maintaining the temperature between 15° C. and 30° C. Stabilize the temperature between 28° C. and 23° C. Add deionized water (7×W)L while maintaining the temperature between about 28° C. and 22° C. Stir the two phase mixture for a period of about 10 to 20 minutes while maintaining the temperature between about 28° C. and 22° C. Stop stirring and allow the phases to separate for a period of at least 30 minutes, then discharge the aqueous phase.

Add to the organic phase deionized water (7×W)L while maintaining the temperature between about 28° C. and 22° C. Stir the two phase mixture for a time period of 10 to 20 minutes while maintaining the temperature between about 28° C. and 22° C., then allow the phases to separate for a time period of at least 30 minutes. Discharge the aqueous phase. Add to the organic phase deionized water (7×W)L while maintaining the temperature between about 28° C. and 22° C. Stir the two phase mixture for a time period of 10 to 20 minutes while maintaining the temperature between about 28° C. and 22° C., then allow the phases to separate for a time period of at least 30 minutes. Discharge the aqueous phase. Sample the aqueous phase and measure the pH. If pH is >7.5, repeat the water wash above. If the pH is <7.5, add n-heptane (5×W)L over a time period of 20 to 30 minutes while maintaining the temperature ≤30° C. Distill the mixture under an approximate pressure of −0.85 bar while maintaining the temperature at ≤50° C. until (4.4×W) kg of the solvent has been distilled. Add n-heptane (6×W)L over a time period of 20 to 30 minutes while maintaining the temperature at ≤50° C. Distill the mixture under an approximate pressure of −0.85 bar while maintaining the temperature at ≤50° C. until (4.4×W)kg of the solvent has been distilled. Add n-heptane (6×W)L over a time period of 20 to 30 minutes while maintaining the temperature at ≤50° C. Sample the mixture and determine the ratio of ethyl acetate: n-heptane by GC analysis. Cool the mixture to a temperature of between about 28° C. and 22° C. under nitrogen atmosphere, then stir the mixture for a time period of at least 2 hours while maintaining the temperature between about 28° C. and 22° C. Filter the product to obtain a wet cake. Wash the wet cake with a mixture of n-heptane (2.8×W)L and ethyl acetate (0.3×W)L. Dry the wet product under vacuum at a temperature of ≤50° C. until LOD<2.0%.

5.1.4 Synthesis of (5)-6-chloro-1-(4-methoxyphenyl)-2,3,4,9-tetrahydro-1H-pyrido[3,4-b]indole (5)-2-acetamido-3-phenylpropanoate Compound of Formula (IIa)

General information.

The reaction depicted in Scheme E was performed in a 300-gallon glass-lined reactor. The chiral acid N-Acetyl-L-phenylalanine was purchased from Paragon (99.5% AUC). Methanol (reagent grade) and ethanol (ethanol, absolute, 200 proof, reagent grade) were used.

Procedure.

Compound of Formula (IVa) (23.1 Kg, 73.8 mol, lot 04-PVC-001X, 1.0 eq) was charged into the 300-gallon reactor followed by chiral acid N-Acetyl-L-phenylalanine (12.2 Kg, 58.9 mol, 0.80 eq) and methanol (547.5 Kg, 693 L, 30×). The mixture was heated to 64±2° C. held for 30 minutes, dissolution confirmed and the solution then cooled on a ramp to 25±2° C. over 3 hours. The slurry was stirred at 25±2° C. for a further 16 hours. The slurry was filtered and the wet cake recharged to the vessel. Ethanol (584.5 Kg, 740 L, 32×) was charged to the vessel and the slurry heated to 78±2° C. Dissolution was confirmed and the solution then cooled on a ramp to 25±2° C. over 3 hours. The slurry was stirred at 25±2° C. for a further 16 hours. The slurry was filtered and the wet cake washed with ethanol (45.5 Kg, 58 L, 2.5×). The wet cake (37.1 Kg) was dried at a set-point of 50° C. for 2 days under vacuum. A total of 15.5 Kg target compound of Formula (IIa) was obtained as an off-white solid. HPLC: 94.6% e.e., (ChiralPak AD-RH column, 150× 4.6 mm, 5 µm; hexanes, isopropanol, diethylamine); Mp=214° C., IR: 3271, 1634, 1541, 1400, 1251, 1179 cm$^{-1}$; $^1$H NMR (300 MHz, DMSO-d6) δ 10.68 (s, 1H), 7.99-8.08 (d, 1H), 7.44-7.45 (d, 1H), 7.13-7.26 (m, 8H), 6.69-7.01 (dd, 1H), 6.88-6.93 (m, 2H), 5.19 (s, 1H), 4.28-4.35 (m, 2H), 3.72 (s, 3H), 2.94-3.15 (m, 3H), 2.66-2.84 (m, 2H), 1.75 (s, 3H). The percent enantiomeric excess (% e.e.) for the compound of Formula (IIa) was calculated using the following formula (wherein the term "(R)-Formula (IIa)" refers to the (R) isomer of the compound of Formula (IIa)):

% e.e. Formula (IIa)=[(AUC$_{Formula\ (IIa)}$−AUC$_{(R)\text{-}Formula\ (IIa)}$)/(AUC$_{Formula\ (IIa)}$+AUC$_{(R)\text{-}Formula\ (IIa)}$)]×100

5.1.5 Seeded Synthesis of (S)-6-chloro-1-(4-methoxyphenyl)-2,3,4,9-tetrahydro-1H-pyrido[3,4-b]indole (S)-2-acetamido-3-phenylpropanoate Compound of Formula (IIa)

Procedure.

To absolute ethanol (2.9 L), add deionized water (0.058 L), then add N-acetyl-(L)-phenylalanine (0.36 kg) while maintaining the temperature between about 28° C. and 22° C. Heat the mixture to reflux over a time period of about 30 to 60 minutes. Cool the mixture to a temperature of between about 58° C. and 52° C. and sample for in-process control (IPC).

To absolute ethanol (19.6 L), add deionized water (0.4 L), then add (±)piperidinoindole (1 kg) while maintaining the temperature between about 28° C. and 22° C. Heat the mixture to reflux and maintain at reflux temperature for a time period of about 50 minutes to 70 minutes and sample for in-process control (IPC).

To the solution of (±)-piperidinoindole, add over a time period of about 10 to 15 minutes 25% of the solution of N-acetyl-(L)-phenylalanine while maintaining the temperature between about 58° C. and 52° C. Seed the reaction mixture with the (S)-piperidinoindole Form B (0.01 kg). Stir for a time period of about 5 minutes at a temperature of between about 58° C. and 52° C. and sample for in-process control (IPC).

Add over a time period of about 2 hours the remaining 75% of the solution N-acetyl-(L)-phenylalanine while maintaining the temperature between about 58° C. and 52° C. Stir the suspension over a time period of about 1 hour while maintaining the temperature between about 58° C. and 52° C. Cool the suspension over a time period of about 2 hours at an approximately linear rate to a temperature of between about 17° C. and 13° C. Then stir the suspension for a time period of about 1 hour while maintaining the temperature between about 17° C. and 13° C. Filter the suspension and wash the product with a mixture of absolute ethanol (5.4 L) and deionized water (0.11 L) previously cooled to a temperature of between about 17° C. and 13° C. to provide a wet product. Add the wet product to a mixture of absolute ethanol (13.5 L) and deionized water (0.28 L) previously cooled to a temperature of between about 24° C. and 20° C. Stir the suspension for a time period of about 2 hours while maintaining the temperature between about 24° C. and 20° C., then cool the suspension to a temperature of between about 17° C. and 13° C. Filter the suspension and wash the product with a mixture of absolute ethanol (5.4 L) and deionized water (0.08 L) previously cooled to a temperature of between about 17° C. and 13° C. Sample the wet product for chiral HPLC analysis.

To a mixture of absolute ethanol (36.3 L) and deionized water (0.7 L) previously adjusted to a temperature of between about 25° C. and 15° C. add the crude, wet (S)-piperidinoindole Ac-Phe product while maintaining the temperature between about 25° C. and 15° C. Heat the mixture to reflux and stir at reflux temperature for a time period of about 50 minutes to 70 minutes, then sample for in-process control (IPC). Cool the suspension over a time period of about 4 hours at an approximately constant rate to a temperature of between about 17° C. and 13° C. Filter the suspension and wash the product with a mixture of absolute ethanol (3.9 L) and deionized water (0.08 L) previously cooled to a temperature of between about 17° C. and 13° C. Sample the wet product for chiral HPLC analysis. Dry the wet product under vacuum at temperature ≤50° C. until LOD≤10.0 wt % (preferentially with an LOD of between about 8.0 wt % and 10.0 wt %).

5.1.6 Synthesis of (S)-4-chlorophenyl 6-chloro-1-(4-methoxyphenyl)-3,4-dihydro-1H-pyrido[3,4-b]indole-2(9H)-carboxylate Compound of Formula (X)

General Information.

The reaction depicted in Scheme E was performed in a 300-gallon glass-lined reactor. Potassium carbonate, anhydrous (reagent grade), ethyl acetate (reagent grade) and heptane (technical grade) were used. 4-chlorophenyl chloroformate (>98%) was purchased from Aldrich. Purified water from the house system was employed for all processing purposes.

Procedure.

A 4.2 wt % solution of potassium carbonate (27.0 Kg, 195 mol, 3.3 eq) in water (592 L) was prepared in a 300 gallon reactor before processing and drummed. To the reactor was charged the compound of Formula (IIa) (30.8 Kg, 59.2 mol, 1.0 eq), ethyl acetate (266.4 Kg, 296 L, 9.6×) and a 4.2 wt % potassium carbonate solution (322.6 Kg, 10.5×). The biphasic slurry was stirred at 25±2° C. for 3 hours and sampled for IPC (Limit: Free of visible solids; pH of aqueous phase <9.0). Once complete the lower aqueous phase was removed and the organic phase washed with water (237 L, 7.7×) to achieve an aqueous phase pH of <7.5. The organic layer was discharged to drums and the vessel rinsed with ethyl acetate (30 Kg, 1×). The batch solution was recharged to the vessel via a 1 micron filter. The batch was distilled under vacuum to ~148 L (4.8×), maximum batch temperature: 30° C. To the reactor was charged 4.2 wt % potassium carbonate solution (322.6 Kg, 10.5×). A 4-Chlorophenyl chloroformate compound of Formula (IIIa) (13.5 Kg, 71.1 mol, 1.2 eq) was charged over 30 minutes while maintaining the batch temperature below 30° C. The slurry was stirred at 25±2° C. for 1 hour and a sample submitted for an in-process check (≤1.0% PV-4 free base relative to PV-5, passed). Once complete, the slurry was filtered and the wet cake washed with water (119 L, 3.9×), followed by ethyl acetate (53.3 Kg, 59 L, 1.9×). The wet cake was sampled for an IPC (Limit: ROI≤0.5%) and passed. The wet cake (39.1 Kg) was dried at a set-point of 50° C. for 2 days under vacuum. A total of 21.9 Kg the target compound of Formula (X) was obtained as an off-white solid (HPLC purity: 98.7% (ChiralPak AD-RH column, 150×4.6 mm, 5 m; 20:80 Mobile Phase B (1 mL diethylamine+1000 mL isopropanol for each liter)/Mobile Phase A (1 mL diethylamine+1000 mL hexanes for each liter); 10 µL injection volume; 1.0 mL/min; 40° C.; detection at 230 nm); Mp=222-223° C.; IR: 3168, 2906, 2767, 1612, 1513, 1421, 1248, 1174, 1032 cm-1; HPLC (std): 14.5 min; HPLC (chiralPAK AD-H, 30% IPA in hexane): 22 min; ES-MS=467.29 (M$^+$H). 1H NMR (300 MHz, CDCl3) δ 7.96 (s, 1H), 7.53 (s, 1H), 7.33 (d, 2H), 7.25 (d, 2H), 7.14 (s, 2H), 7.06 (dd, 2H), 6.84 (d, 2H), 6.46 (s, 1H), 4.46 (dd, 1H), 3.79 (s, 3H), 3.32 (m, broad, 1H), 2.99 (m, broad, 1H), 2.82-2.89 (dd, 1H).

5.1.7 Alternate Synthesis of (S)-4-chlorophenyl 6-chloro-1-(4-methoxyphenyl)-3,4-dihydro-1H-pyrido[3,4-b]indole-2(9H)-carboxylate Compound of Formula (X)

Procedure.

To a vigorously stirred suspension of Formula (IIa) (200 g corrected from 220.32 g, after correction of ethanol (9%)

with KF (0.23%)) in MEK (4 L) at 30±3° C. was added 8.4% aqueous potassium carbonate (1048 g). The suspension was stirred at 30±3° C. for a time period of at least 60 minutes. The biphasic mixture was IPC sampled for solids and pH analysis (Limit: free of visible solids, pH of aqueous phase >9.0). The layers were allowed to separate and the organic phase was washed with 8.4% aqueous solution of potassium carbonate (1048 g). The organic phase was then recharged to the vessel via a 1-micron filter. The vessel was charged with 8.4% aqueous potassium carbonate (1048 g). Then 4-chlorophenyl chloroformate (77.13 g, 1.05 eq) was charged over a time period of 30 minutes while maintaining the bath temperature at 40±2° C. The batch was stirred at about 40±2° C. for an additional 2 hours, then sampled IPC (Limit: NMT 0.1% Formula (IIa) relative to Formula (X)). The layers were allowed to separate and the organic phase was washed twice with purified water (2×720 g). The organic layer was distilled under atmospheric conditions at about 85-90° C. to a volume of about 4× (about 800 mL MEK) and sampled for KF. The batch was diluted with MEK (3.2 L), redistilled under atmospheric conditions at about 85° C.-90° C. to a volume of about 4× (about 800 mL MEK) and sampled for KF. These steps were repeated until a proper KF (below 0.5%) for the residual organic layer was achieved. The organic layer was then cooled to RT (25±2° C.) and diluted with heptanes (1.35 Kg) over a time period of about 1 hour.

The slurry was stirred at 25±2° C. over a time period of about 1 hour. The product was isolated by filtration to provide a wet cake. The wet cake was washed with a mixture of heptane (130 g) and ethyl acetate (260 g), dried under suction for 30 min, then dried at 50±3° C. under vacuum for 13 h to yield 146.5 g of pure Formula (X) (yield: 90%; LCAP: 99.8%; chiral purity: 100%).

5.1.7.1 Removal of Entrained Compound of Formula (IIa)

The example demonstrates methods to remove entrained compound of Formula (IIa) from the reaction product obtained in the procedure described for the synthesis of the compound of Formula (X) in Section 5.1.5.

Evaluation on Small Scale.

A series of experiments were conducted to provide a suitable rework procedure to remove entrained compound of Formula (IIa). A representative list of experiments is given in Table 1. Solvent, batch temperature, time, and solvent volume were all found to be critical to the effectiveness of the rework procedure. The experiment in which the compound of Formula (X), obtained by the procedure described hereinabove, was refluxed in 8 volumes of ethyl acetate for 3 hours provided consistent yield and purity, and was used as the basis for the pilot plant rework procedure.

TABLE 1

Development of Rework Procedure for the Compound of Formula (X)

| Solvent system (Volumes) | Temperature | Time (h) | Impurity RRT- 0.48 (area %) | Yield (%) |
|---|---|---|---|---|
| EtOAc (4) | ambient | 1 | 1.05 | 88.3 |
| EtOAc (4) | reflux | 1 | 0.48 | 90.0 |
| EtOAc (8) | reflux | 1 | 0.38 | 83.3 |
| EtOAc (16) | reflux | 1 | 0.31 | 74.8 |
| EtOAc (8) | reflux | 3 | 0.16 | 88.2 |
| EtOH (15) | reflux | 1 | 0.47 | 93.0 |

TABLE 1-continued

Development of Rework Procedure for the Compound of Formula (X)

| Solvent system (Volumes) | Temperature | Time (h) | Impurity RRT- 0.48 (area %) | Yield (%) |
|---|---|---|---|---|
| McOH (4) | reflux | 1 | 1.02 | 91.3 |
| DCM (4) | reflux | 1 | 0.43 | 79.4 |
| Acetone (4) | reflux | 1 | 0.25 | 84.5 |
| Water (4) | reflux | 1 | 1.10 | 96.7 |
| 1M HCl (4) | ambient | 1 | 1.10 | 88.0 |

Plant Scale Experiment.

General Information.

Ethyl acetate (reagent grade) was used.

Procedure.

To a 100 gallon reactor was charged the compound of Formula (X) (21.6 Kg, 46.2 mol) followed by ethyl acetate (157.3 Kg, 175 L, 8.1×). The slurry was warmed to 77±2° C. and stirred for 3 hours. The slurry was cooled to 20-23° C. over about 1.5 hours. The slurry was stirred at 20-23° C. for about 4 hours. The slurry was filtered and the wet cake washed with ethyl acetate (19.7 Kg, 21.9 L, 1×). The wet cake was sampled for IPC (Limit: ROI≤0.5%). The wet cake was dried at ambient for 2 hours, 30±2° C. for 2 hours, 40±2° C. for 2 hours and 50° C. until dry (2 days) under vacuum. A total of 17.7 Kg of the compound of Formula (X) was obtained as an off-white solid (HPLC; purity 99.5%, >99.9% e.e.).

The chiral purity was calculated as % enantiomeric excess following HPLC analysis (column: ChiralPak AD-RH, 150× 4.6 mm, 5 m; mobile phase: hexanes (0.1% v/v diethylamine) and isopropanol (0.1% v/v diethylamine) (80:20); column temperature: 40° C.; flow rate: 1.0 mL/min; Detection: UV, 230 nm). The retention times of (R)-Formula (IVa) and (S)-Formula (IVa) are 11.3 min and 22.2 min, respectively. The percent enantiomeric excess (% e.e.) for the compound of Formula (X) was calculated using the following formula (wherein the term "(R)-Formula (X)" refers to the (R) isomer of the compound of Formula (X)):

$$\% \text{ e.e. Formula } (X) = [(AUC_{Formula\ (X)} - AUC_{(R)\text{-}Formula\ (X)})/(AUC_{Formula\ (X)} + AUC_{(R)\text{-}Formula\ (X)PV\text{-}5})] \times 100$$

5.2 Chiral Resolution of 6-chloro-1-(4-methoxyphenyl)-2,3,4,9-tetrahydro-1H-pyrido[3,4-b]indole Compound of Formula (IVa)

This example demonstrates that ethanol with a 2-5% v/v water content delivers (S)-6-chloro-1-(4-methoxyphenyl)-2,3,4,9-tetrahydro-1H-pyrido[3,4-b]indole (S)-2-acetamido-3-phenylpropanoate compound of Formula (IIa) with an optical purity of greater than about 98%.

Procedure.

6-chloro-1-(4-methoxyphenyl)-2,3,4,9-tetrahydro-1H-pyrido[3,4-b]indole compound of Formula (IVa) (1 eq) and N-acetyl-L-phenylalamine (0.51 eq) were dissolved in a various mixtures of 260 ml of ethanol and water (as shown in Table 2) content and heated under reflux for 18 h. The mixture was then cooled, and filtrated to obtain (S)-6-chloro-1-(4-methoxyphenyl)-2,3,4,9-tetrahydro-1H-pyrido[3,4-b]indole (S)-2-acetamido-3-phenylpropanoate compound of Formula (IIa) in the yields and enantiomeric purity reported in Table 2. The chiral purity is calculated as % enantiomeric excess following HPLC analysis (column: ChiralPak AD-H, 150×4.6 mm, 5 μm; mobile phase: isopropanol:hexanes:diethylamine=20:80:1; column temperature: 25° C.; flow rate: 1.0 mL/min; Detection: UV, 230 nm). The retention times of (R)-Formula (IIa) and compound of Formula (IIa) are 0.71 min and 1.00 min, respectively. The percent enantiomeric excess (% e.e.) for the compound of Formula (IIa) was calculated using the following formula (wherein the term "(R)-Formula (IIa)" refers to the (R) isomer of the compound of Formula (IIa)):

% e.e. Formula (IIa)=[(AUC$_{Formula\ (IIa)}$−AUC$_{(R)\text{-}Formula\ (IIa)}$)/(AUC$_{Formula\ (IIa)}$+AUC$_{(R)\text{-}Formula\ (IIa)}$)]×100

TABLE 2

| Exp. # | Scale (g) | N—Ac-L-Phenylalanine (eq.) | EtOH (mL) | Amount of water (v/v) | Yield (%) | Chiral Purity (e.e. %) |
|---|---|---|---|---|---|---|
| 1 | 20 | 0.51 | 260 | None | 45.8 | 97.9 |
| 2 | 20 | 0.51 | 260 | 1% H$_2$O | 45.5 | 97.8 |
| 3 | 50 | 0.51 | 260 | 2% H$_2$O | 45.0 | 99.4 |
| 4 | 110 | 0.51 | 260 | 2% H$_2$O | 45.7 | 99.4 |
| 5 | 20 | 0.51 | 260 | 3% H$_2$O | 45.5 | 99.1 |
| 6 | 20 | 0.51 | 260 | 4% H$_2$O | 45.2 | 99.0 |
| 7 | 20 | 0.51 | 260 | 5% H$_2$O | 44.0 | 98.6 |

Those skilled in the art will recognize, or be able to ascertain using no more than routine experimentation, many equivalents to the specific embodiments described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

What is claimed is:

1. A process for preparing a compound of Formula (IIa):

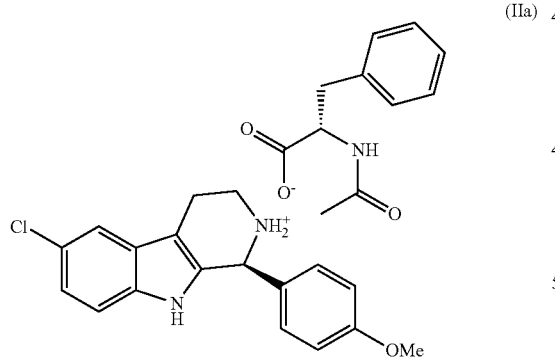

(IIa)

comprising the steps of:
i) preparing a mixture by adding 2% water to absolute ethanol then adding N-acetyl-(L) phenylalanine;
ii) heating the mixture to reflux;
iii) cooling the refluxed mixture from step ii) to a temperature between about 58° C. and 52° C.;
iv) preparing a solution by adding 2% water to absolute ethanol then adding a compound of Formula (IVa):

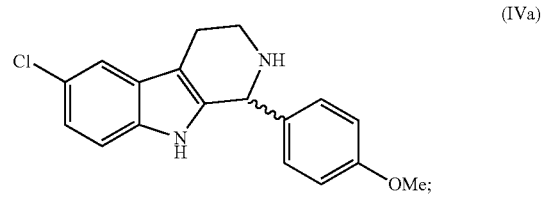 [SMILES: COc1ccc(C2NCCc3c2[nH]c2ccc(Cl)cc32)cc1]

(IVa)

v) heating the solution to reflux;
vi) cooling the refluxed solution from step v) to a temperature between about 58° C. and 52° C.;
vii) preparing a reaction mixture by adding 0.1 equivalents of N-acetyl-(L) phenylalanine from the mixture from step iii) to one equivalent of Formula (IVa) from the solution from step vi) while maintaining a temperature between about 58° C. and 52° C.;
viii) seeding the reaction mixture by adding (S)-piperindinoindole Form B, wherein (S)-piperindinoindole Form B is a crystalline form of the compound of Formula (IIa), and stirring for about 5 minutes;
ix) forming a suspension by adding an additional 0.4 equivalents of N-acetyl-(L)-phenylalinine from the mixture from step iii) to the reaction mixture from step viii) while maintaining a temperature of between about 58° C. and 52° C.;
x) cooling the suspension from step ix) to a temperature of between about 17° C. and 13° C. at a linear rate over a period of about 2 hours;
xi) stirring the cooled suspension from step x) while maintaining the temperature between about 17° C. and 13° C. for about 1 hour; and
xii) filtering the stirred suspension of step xi) and washing with a mixture of absolute ethanol and 2% water.

2. The process of claim 1, wherein the refluxing in step ii) is conducted over a time period of about 30 to about 60 minutes.

3. The process of claim 1, wherein the refluxing in step v) is conducted over a time period of about 50 to about 70 minutes.

4. The process of claim 1, wherein in step vii) the mixture of step ii) is added to the solution of step v) over a time period of about 15 minutes.

5. The process of claim 1, wherein in step ix) the mixture of step ii) is added to the reaction mixture solution of step viii) over a time period of about 2 hours.

6. The process of claim 1, wherein the concentration of N-acetyl-(L)-phenylalanine in the mixture of step i) is 0.17 M, and the concentration of Formula (IVa) in the solution of step iv) is 0.16 M.

* * * * *